United States Patent
Lacoste et al.

(10) Patent No.: US 10,472,248 B2
(45) Date of Patent: Nov. 12, 2019

(54) METHOD FOR MANUFACTURING CALCIUM ZINCATE CRYSTALS, AND THE USES THEREOF

(71) Applicant: EASYL, Bonneville (FR)

(72) Inventors: Francois Lacoste, Neuilly sur Seine (FR); Julien Thiel, Arbusigny (FR)

(73) Assignee: EASYL, Bonneville (FR)

( * ) Notice: Subject to any disclaimer, the term of this patent is extended or adjusted under 35 U.S.C. 154(b) by 0 days.

(21) Appl. No.: 15/563,237

(22) PCT Filed: Mar. 31, 2016

(86) PCT No.: PCT/FR2016/050736
§ 371 (c)(1),
(2) Date: Sep. 29, 2017

(87) PCT Pub. No.: WO2016/156749
PCT Pub. Date: Oct. 6, 2016

(65) Prior Publication Data
US 2018/0086646 A1    Mar. 29, 2018

(30) Foreign Application Priority Data
Apr. 3, 2015 (FR) ...................................... 15 52884

(51) Int. Cl.
*C01G 9/00*    (2006.01)
*C01F 11/00*   (2006.01)
(Continued)

(52) U.S. Cl.
CPC ............... *C01G 9/00* (2013.01); *A01N 59/16* (2013.01); *B01D 9/0063* (2013.01); *B01J 23/06* (2013.01);
(Continued)

(58) Field of Classification Search
CPC ......... C01G 9/00; C01F 11/00; B02C 17/163; H01M 4/224; H01M 4/26
See application file for complete search history.

(56) References Cited

U.S. PATENT DOCUMENTS

| 3,607,409 A | 9/1971 | Robert et al. |
| 2002/0134964 A1* | 9/2002 | Christian ............... B82Y 30/00 252/182.1 |

(Continued)

FOREIGN PATENT DOCUMENTS

| CN | 1482698 A * | 3/2004 |
| CN | 1 595 688 A | 3/2005 |

(Continued)

OTHER PUBLICATIONS

Raven Systems, Hardness conversion table, pulication date Aug. 2015.*

(Continued)

*Primary Examiner* — Jun Li
(74) *Attorney, Agent, or Firm* — Young & Thompson

(57) ABSTRACT

Disclosed is a method for manufacturing calcium zincate crystals including: placing calcium hydroxide$_2$ and zinc oxide, one of the precursors thereof, or one of the water mixtures thereof in a starting suspension, the mass ratio of water to calcium hydroxide and zinc oxide, or one of the precursors or mixtures thereof, being greater than or equal to 1; milling the starting suspension to an ambient temperature less than or equal to 50° C. in a wet-phase three-dimensional micro-ball mill for a residence time less than or equal to 15 minutes and in particular from 5 to 25 seconds; recovering a calcium zincate crystal suspension coming out of the mill; and optionally, concentrating or drying the calcium zincate crystal suspension so as to obtain a calcium zincate crystal powder. Also disclosed are uses associated with the calcium (Continued)

zincate crystals obtained according to the method described above.

20 Claims, 6 Drawing Sheets

(51) Int. Cl.

| | | |
|---|---|---|
| *B01D 9/00* | (2006.01) | |
| *A01N 59/16* | (2006.01) | |
| *B01J 23/06* | (2006.01) | |
| *H01M 4/08* | (2006.01) | |
| *H01M 4/24* | (2006.01) | |
| *H01M 4/26* | (2006.01) | |
| *H01M 4/58* | (2010.01) | |
| *H01M 4/62* | (2006.01) | |
| *B01J 37/04* | (2006.01) | |
| *B01J 37/08* | (2006.01) | |
| *B01J 35/00* | (2006.01) | |
| *B01J 37/00* | (2006.01) | |
| *B02C 17/16* | (2006.01) | |
| *B02C 17/18* | (2006.01) | |

(52) U.S. Cl.
CPC ......... *B01J 35/002* (2013.01); *B01J 37/0036* (2013.01); *B01J 37/04* (2013.01); *B01J 37/08* (2013.01); *B02C 17/163* (2013.01); *B02C 17/183* (2013.01); *C01F 11/00* (2013.01); *H01M 4/08* (2013.01); *H01M 4/244* (2013.01); *H01M 4/26* (2013.01); *H01M 4/5825* (2013.01); *H01M 4/62* (2013.01); *B01D 2009/0086* (2013.01); *C01P 2002/72* (2013.01); *C01P 2004/03* (2013.01); *C01P 2004/51* (2013.01); *C01P 2004/61* (2013.01); *C01P 2006/10* (2013.01)

(56) References Cited

U.S. PATENT DOCUMENTS

| | | | |
|---|---|---|---|
| 2004/0166412 A1 | 8/2004 | Bugnet et al. | |
| 2011/0126899 A1* | 6/2011 | Abe | C23C 14/3414 136/256 |
| 2015/0056258 A1* | 2/2015 | Richardson | A01N 59/20 424/409 |
| 2016/0115321 A1* | 4/2016 | Hasegawa | C09D 201/00 106/14.05 |

FOREIGN PATENT DOCUMENTS

| | | |
|---|---|---|
| CN | 101264924 | 9/2008 |
| SU | 116812 A1 | 11/1958 |
| WO | 98/44579 A2 | 10/1998 |
| WO | 03/015197 A2 | 2/2003 |
| WO | 2004/013064 A2 | 2/2004 |
| WO | 2006/032208 A1 | 3/2006 |
| WO | 2010/112641 A1 | 10/2010 |

OTHER PUBLICATIONS

Machine translation of CN1482698, pulication date Mar. 2004.*
X-M Zhu: "Structural and electrochemical characterization of mechanochemically synthesized calcium zincate as rechargeable anodic materials", Journal of Applied Electrochemistry, vol. 33, 2003, pp. 607-612, XP001211650, DOI: doi:10.1023/A:1024999207178.
Huabin Yang et al: "Calcium Zincate Synthesized by Ballmilling as a Negative Material for Secondary Alkaline Batteries", Journal of the Electrochemical Society, vol. 151, No. 12, Jan. 1, 2004 (Jan. 1, 2004), pp. A2126, XP055248646, ISSN: 0013-4651, DOI: 10.1149/1.1815158.
Eljka Kesi et al: "Mechanochemical preparation and characterization of CaOZnO used as catalyst for biodiesel synthesis", Applied Catalysis A: General, Elsevier Science, Amsterdam, NL, vol. 427, Mar. 22, 2012 (Mar. 22, 2012), pp. 58-65, XP028480472, ISSN: 0926-860X, [retrieved on Apr. 1, 2012], DOI: 10.1016/J.APCATA.2012.03.032.
N.M. Gomez-Ortiz et al: "Antifungal activity of Ca[Zn(OH)3]2.2H2O coatings for the preservation of limestone monuments: An in vitro study", International Biodeterioration and Biodegradation, vol. 91, Mar. 27, 2014 (Mar. 27, 2014), GB, pp. 1-8, XP055248857, ISSN: 0964-8305, DOI: 10.1016/j.ibiod.2014.02.005.
Ram A. Sharma: "Physico-Chemical Properties of Calcium Zincate", Journal of the Electrochemical Society, Nov. 1986 (Nov. 1, 1986).
Jingxian Yu: "A study of calcium zincate as negative electrode material for secondary batteries", Journal of Power Sources, vol. 103, 2001, pp. 93-97, XP004324002, DOI: doi:10.1016/S0378-7753(01)00833-3.
Shengwei Wang: "Study of calcium zincate synthesized by solid-phase synthesis method without strong alkali", Material Chemistry and Physics, vol. 112, 2008, pp. 603-606.
Jm Rubio Caballero: "Calcium zincate as precursor of active catalysts for biodiesel production under mild conditions", Applied Catalysis B : Environmental, vol. 91, 2009, pp. 339-346, XP026393353.
C.S. Xavier et al.: "A new processing method of CaZn2(OH)6.2H2O powders: Photoluminescence and growth mechanism", Solid State Sciences, Solid State Sciences 11 (2009) 2173-2179.
International Search Report, dated Jul. 28, 2016, from corresponding PCT/FR2016/050736 application.

* cited by examiner

Fig.1
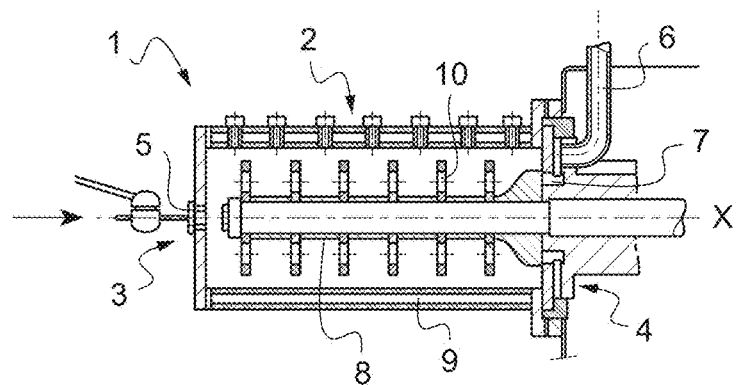
Fig.2
a) 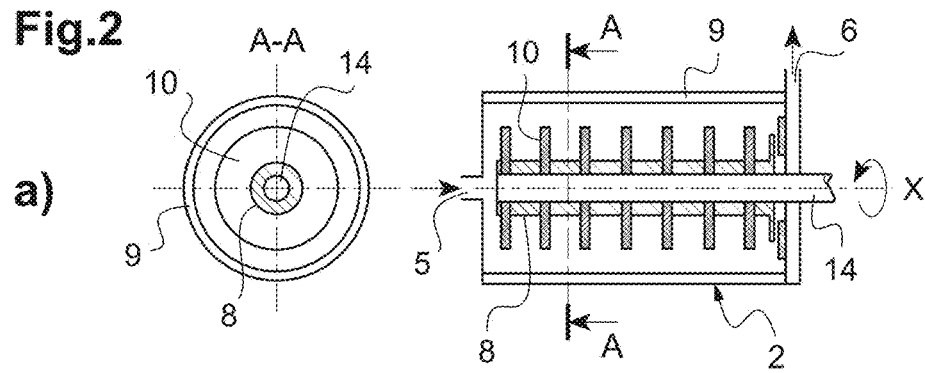
b) 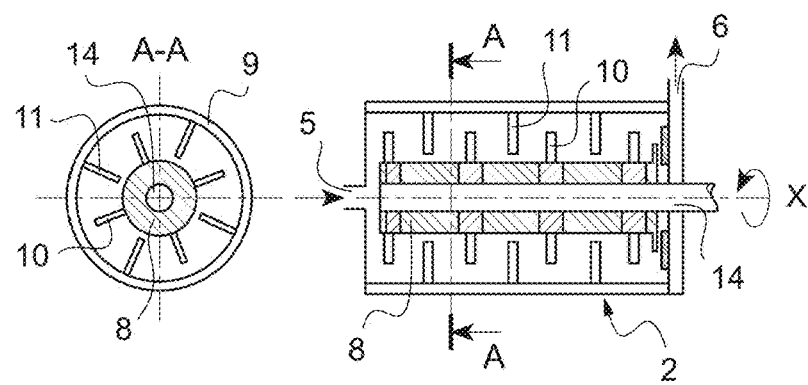
c) 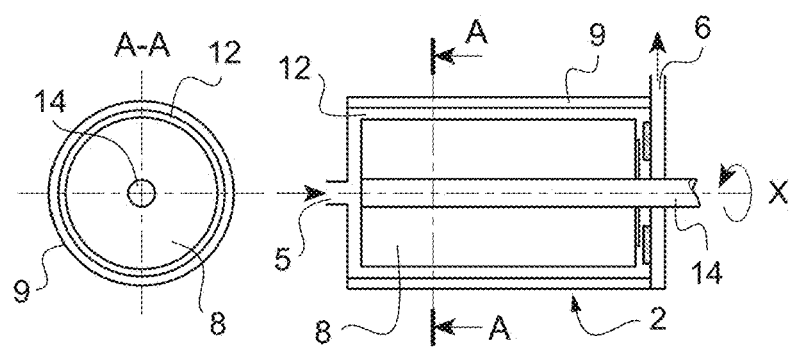

Fig.6
| | Billes 0.5mm | |
|---|---|---|
| | 30l/h | 90l/h |
| 300g/l | (a)<br>Dx (10) : 4.75 µm<br>Dx (50) : 9.02 µm<br>Dx (90) : 15.1 µm<br>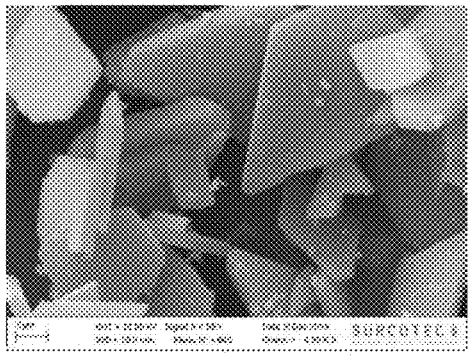 | (b)<br>Dx (10) : 5.03 µm<br>Dx (50) : 9.97 µm<br>Dx (90) : 16.9 µm<br>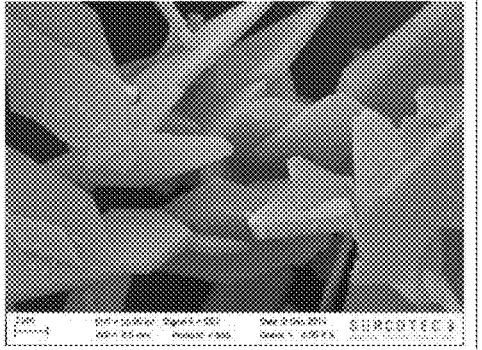 |
| 600g/l | (c)<br>Dx (10) : 6.12 µm<br>Dx (50) : 11.1 µm<br>Dx (90) : 17.9 µm<br>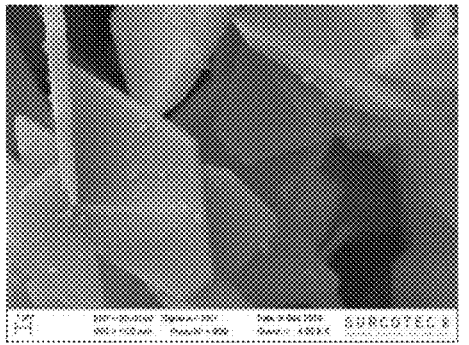 | (d)<br>Dx (10) : 6.36 µm<br>Dx (50) : 12.8 µm<br>Dx (90) : 21.1 µm<br>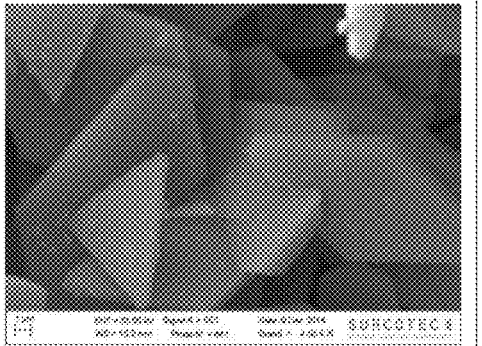 |

Fig.7

| | Billes 1mm | |
|---|---|---|
| | 30l/h | 90l/h |
| 300g/l | (a)<br>Dx (10) : 3.48 μm<br>Dx (50) : 7.44 μm<br>Dx (90) : 13.6 μm | (b)<br>Dx (10) : 3.31 μm<br>Dx (50) : 6.97 μm<br>Dx (90) : 12.5 μm |
| 600g/l | (c)<br>Dx (10) : 4.60 μm<br>Dx (50) : 8.99 μm<br>Dx (90) : 15.2 μm | (d)<br>Dx (10) : 4.31 μm<br>Dx (50) : 8.40 μm<br>Dx (90) : 14.2 μm |

Fig.8
| | Billes 2mm | |
|---|---|---|
| | 30l/h | 90l/h |
| 300g/l | (a)<br>Dx (10) : 3.98 μm<br>Dx (50) : 7.59 μm<br>Dx (90) : 12.6 μm<br>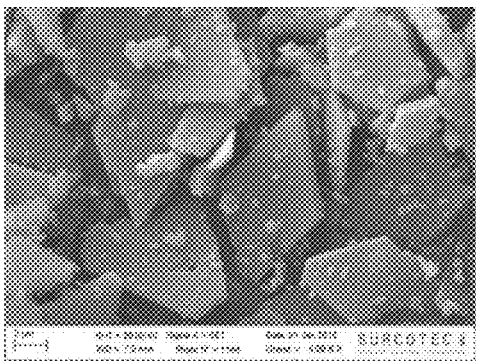 | (b)<br>Dx (10) : 3.98 μm<br>Dx (50) : 7.66 μm<br>Dx (90) : 12.7 μm<br>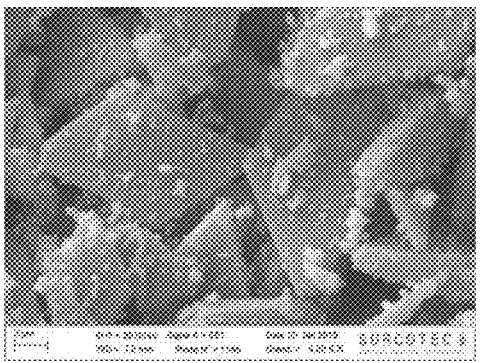 |
| 600g/l | (c)<br>Dx (10) : 4.68 μm<br>Dx (50) : 8.80 μm<br>Dx (90) : 14.5 μm<br>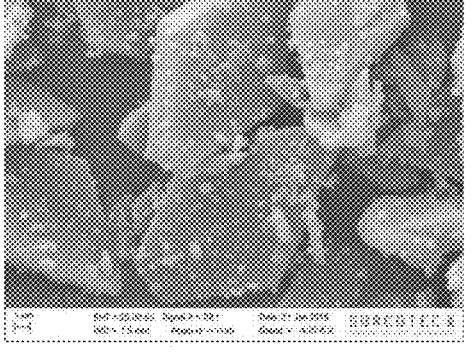 | (d)<br>Dx (10) : 5.01 μm<br>Dx (50) : 9.33 μm<br>Dx (90) : 15.3 μm<br>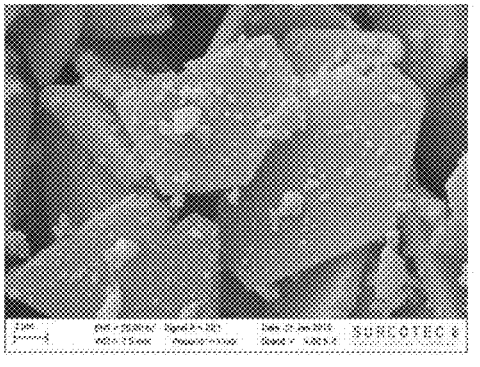 |

METHOD FOR MANUFACTURING CALCIUM ZINCATE CRYSTALS, AND THE USES THEREOF

FIELD OF THE INVENTION

The present invention relates to a process for manufacturing calcium zincate crystals.

In particular, the present invention relates to a process for manufacturing calcium zincate crystals performed by micromilling, in a large excess of water and especially without particular heating, of a mixture comprising at least zinc oxide and calcium hydroxide.

The present invention also relates to a powder or a suspension of calcium zincate crystals obtained according to the process as defined above.

The invention also relates to the uses of the zincate crystals obtained with the abovementioned process for manufacturing: a zinc anode of an alkaline electrochemical generator, a heterogeneous catalyst for the production of biodiesel or an antifungal product.

PRIOR ART

Calcium zincate, of formula $Ca[Zn(OH)_3]_2 \cdot 2H_2O$, has been the subject of extensive research in view of its use in very varied fields, especially that of alkaline electrochemical generators, such as nickel (Ni)/Zinc (Zn) alkaline accumulators. Calcium zincate may especially be incorporated into the active mass of the zinc electrode in order to form such alkaline batteries.

To this end, many synthetic processes have been investigated in the last about 60 years in the prior art.

A first proposed approach consists in synthesizing calcium zincate crystals chemically, in an alkaline medium.

SU116812 (referred to hereinbelow as "Zhulidov") from 1958 describes a process for the electrolytic production, in a tank equipped with zinc anodes and cathodes and containing a caustic soda solution, consisting in reacting a concentrated suspension of calcium hydroxide with zinc oxide released by electrolysis. The temperature of the bath is limited to 80° C. and the water vaporized is regularly compensated for by addition. The duration of the operation is not indicated. The product obtained is washed and decanted several times to remove the caustic soda. The zincate content of the final product is between 35% and 40%, without details being given regarding the measuring method.

The publication by Ram A. Sharma entitled "Physicochemical Properties of Calcium Zincate" published by the "Journal of the electrochemical society", November 1986 (referred to hereinbelow as "Sharma") describes the preparation of pure calcium zincate crystals by reacting, in potassium hydroxide (KOH) at 20% by weight, dissolved zinc oxide with calcium hydroxide added gradually. The entire reaction lasts about 24 hours in total. The product is washed and decanted several times to remove the potassium hydroxide. The final product is constituted of pure lamellar calcium zincate crystals, generally having a very characteristic tetragonal form and the mean size of which obtained is about 30 µm. This process is often referenced since it is relatively easy to perform in a laboratory and makes it possible to obtain a pure and well-characterized product (the X-ray diffraction, XRD, spectrum having characteristic peaks at $2\theta=14.14°$ and $28.57°$).

Other publications describe similar processes for synthesizing calcium zincate crystals. Mention may be made especially of the following documents: U.S. Pat. No. 3,607,409, WO 98/44579, WO 2006/032208, or the publication by C. S. Xavier entitled "A new processing method of CaZn$(OH)_2 \cdot 2H_2O$ powders: photoluminescence and growth mechanism" published by Elsevier and appearing in the scientific review "Solid State Sciences 11" (2009) 2173-2179; or the publication by Jinhao Hao entitled "A Facile Route for the Preparation of Calcium Zincate and its Application in Ni—Zn Batteries" published by the scientific review "Journal of the Electrochemical Society", 161 (5) A704-A707 (2014).

A second approach proposed in the prior art for manufacturing calcium zincate crystals consists in synthesizing these crystals thermochemically.

The publication by Shengwei Wang entitled "Study of calcium zincate synthesized by solid-phase synthesis method without strong alkali" published in the review "Material Chemistry and Physics 112 (2008) 603-606 ("Wang"), describes a process for preparing calcium zincate by simple heating at 75° C., for a period of 12 hours, of a suspension comprising a mixture in stoichiometric proportions of calcium hydroxide and zinc oxide in water. The product obtained, after a succession of one or two washes and filtrations with distilled water, is constituted mainly of well-formed crystals whose mean size is about 45 µm.

However, the processes for synthesizing calcium zincate obtained chemically or thermochemically have the drawbacks of requiring:

- a relatively long reaction time (for example 24 hours for the Sharma or Jinhao Hao document, or even 2 or 3 days for WO 98/44579);
- numerous steps, including washing and decantation steps, in order to remove the undesired side products, such as potassium hydroxide or caustic soda, which are expensive and consume water, which also makes these processes impracticable on an industrial scale and environmentally unfriendly;
- or even of requiring a step of heating above 40° C. (75° C. for 12 hours for the Wang publication, 40 to 80° C. for WO2006/032208, or even 130° C. for the C. S. Xavier publication).

A final approach for manufacturing calcium zincate crystals consists in synthesizing them via mechanosynthesis.

The publication by Huabin Yang entitled "Calcium Zincate Synthesized by Ballmilling as a Negative Material for Secondary Alkaline Batteries" appearing in the "Journal of the Electrochemical Society", 151 (12) A2126-A2131, 2004 (referred to hereinbelow as "Yang"), discloses a process for preparing calcium zincate via mechanosynthesis by milling, in a steel bowl with steel balls 10 and 20 mm in diameter, a mixture in stoichiometric proportions of calcium hydroxide and zinc oxide, with addition of water in a content strictly necessary for the formation of the zincate. The mass of the balls is equal to four times that of the milled mixture. The rotation speed of the bowl is 300 rpm and the milling lasts for 9 hours. The author notes that the increase in temperature during this intense milling may contribute toward facilitating the synthesis. Analysis of the X-ray diffraction (XRD) spectrum of the final product indicates that the conversion into calcium zincate of the initial mixture is complete and that the relative intensities of the various lines of this spectrum are very close to those obtained via the process described in the "Sharma" publication. Given the intense milling performed on this zincate, it is not surprising that its mean particle size is about 3 µm.

The prior art also discloses the publication by X-M Zhu entitled "Structural and electrochemical characterization of mechanochemically synthesized calcium zincate as rechargeable anodic materials" appearing in the "Journal of Applied Electrochemistry 33: 607-612", 2003. Said publication also describes a process for preparing calcium zincate via mechanosynthesis. This process consists in milling in an agate bowl with agate balls 10 mm in diameter a mixture in stoichiometric proportions of calcium hydroxide and zinc oxide, with water in a content strictly necessary for the formation of the calcium zincate. The mass of the balls is equal to four times that of the milled mixture and the rotation speed is 70 rpm. The author studied the change in the X-ray diffraction (XRD) spectrum of the final product as a function of the duration of milling. It appears that at least two hours are needed to make the lines corresponding to the initial calcium hydroxide and zinc oxide disappear, and the milling needs to be continued for 48 hours to obtain a spectrum in which the relative intensities of the lines are comparable to those obtained via the processes described in "Sharma". Comparison of the rate of decomposition in potassium hydroxide at 20% by weight of the calcium zincates obtained after short or long milling operations reveals that the calcium zincates obtained after long milling are more stable than those that have only undergone short milling.

The known mechanosynthesis processes thus have the drawbacks of requiring, just like the chemical or thermal processes, an extremely long reaction time, i.e. from 9 to 18 hours for Yang and 48 hours for Zhu and consequently of being difficult to transpose to the industrial scale.

Thus, although, since 1958, much research has been performed in order to provide a process for manufacturing calcium zincate crystals which is easy to perform while at the same time being industrializable, none of these research efforts has made it possible to date to develop such a process.

There is thus a real need for a novel process for manufacturing calcium zincate crystals that allows the manufacture of such crystals rapidly, while at the same time reducing the risks of pollution and the costs, thus making the process usable on an industrial scale.

The aim of the present invention is, consequently, to propose a novel process for manufacturing calcium zincate crystals which at least partly avoids the abovementioned drawbacks.

SUMMARY OF THE INVENTION

To this end, one subject of the present invention is a process for manufacturing calcium zincate crystals which comprises at least the following steps:
  placing in suspension at least: calcium hydroxide (Ca(OH)$_2$) and zinc oxide (ZnO) or a precursor thereof, such as ZnO$_2$ or Zn(OH)$_2$, or a mixture thereof, with water, referred to as the "starting suspension", the mass ratio of (water):(calcium hydroxide+zinc oxide, a precursor thereof or a mixture thereof) being greater than or equal to 1, preferably ranging from 2 to 15 and in particular ranging from 3 to 5;
  milling said starting suspension at an ambient temperature of less than or equal to 50° C., preferably less than or equal to 35° C., in a three-dimensional wet-phase microball mill for a residence time of less than or equal to 15 minutes, preferably less than or equal to 1 minute, and ranging especially from 5 to 25 seconds and in particular from 10 to 20 seconds;
  recovering at the mill outlet a suspension of calcium zincate crystals, and
  optionally, said suspension of calcium zincate crystals is concentrated or dried so as to obtain a powder of calcium zincate crystals.

For the rest of the description, unless specifically mentioned otherwise, the indication of a range of values "from X to Y" or "between X and Y", in the present invention, is understood as including the values X and Y.

A subject of the present invention is also a powder or a suspension of calcium zincate crystals obtained according to the process described above, characterized in that the crystals are in microlozenge form and have the following population distributions as a function of their particle size: 5 µm≤D$_x$50≤13 µm and 10 µm≤D$_x$90≤20 µm measured with a laser particle size analyzer in liquid mode. As a result of the entrainment current which orients the particles in the direction of the length, the values measured by the particle size analyzer correspond to their major axes.

A subject of the present invention is also the use of a powder or a suspension of calcium zincate crystals as described above for manufacturing a zinc anode of an alkaline electrochemical generator.

Another subject of the present invention is the use of the powder or the suspension of calcium zincate crystals as described above for manufacturing a heterogeneous catalyst for the production of biodiesel, the calcium zincate crystals being calcined beforehand at a temperature of greater than or equal to 400° C.

Finally, the present invention relates to the use of the powder or suspension of calcium zincate crystals as described above as an antifungal product.

DETAILED DESCRIPTION THE INVENTION

The invention will be understood more clearly and other aims, details, characteristics and advantages thereof will emerge more clearly on reading the following description of implementation examples, with reference to the attached figures in which:

FIG. 1 represents a view in cross section along the longitudinal axis XX of a three-dimensional wet-phase microball mill, according to one implementation variant that is suitable for performing the process according to the invention;

FIG. 2 represents views in cross section along the axis XX and the axis AA, of variants of three-dimensional wet-phase microball mills according to FIG. 1 in which: (a) the agitator is a disk agitator, (b) the agitator comprises fingers and (c) the milling chamber is annular;

FIG. 6 represents scanning electron microscopy (SEM) photographs of calcium zincate crystals obtained according to the process of the invention using a ball diameter of 500

Figure 3:
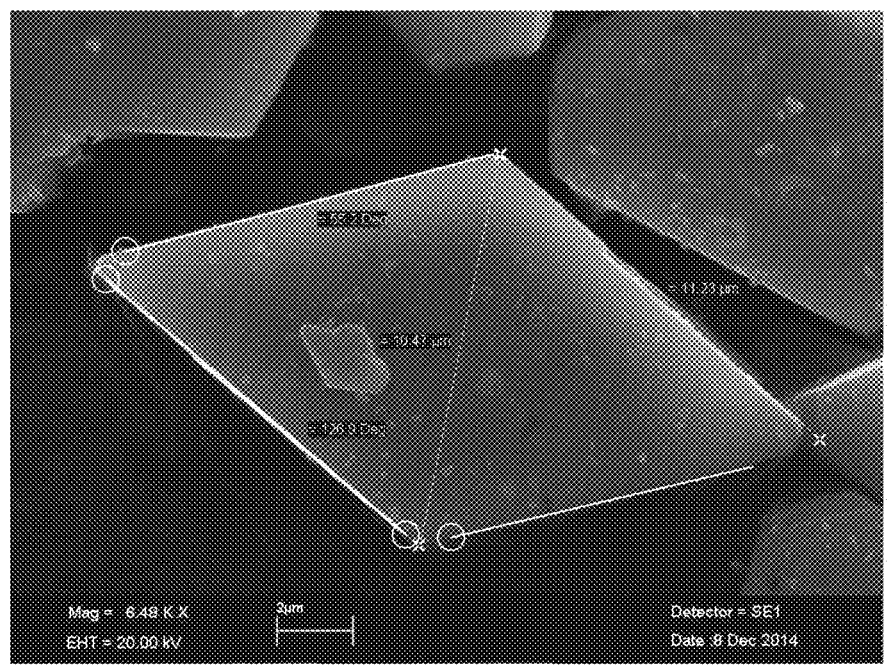
FIG. 3 is a scanning electron microscopy (SEM) photograph of calcium zincate crystals obtained according to a process of the invention using the following parameters: starting suspension comprising 300 g/L of starting materials (Ca(OH)$_2$+ZnO), a flow rate of passage of the starting suspension through the mill of 30 L/h and a ball diameter of 500 µm.

μm and the following parameters: (a) concentration of starting materials 300 g/L/passage flow rate of 30 L/h; (b) concentration of starting materials 300 g/L/passage flow rate of 90 L/h; (c) concentration of starting materials 600 g/L/passage flow rate of 30 L/h; (d) concentration of starting materials 600 g/L/passage flow rate of 90 L/h;

FIG. 7 represents scanning electron microscopy (SEM) photographs of calcium zincate crystals obtained according to the process of the invention using a ball diameter of 1 mm and the following parameters: (a) concentration of starting materials 300 g/L/passage flow rate of 30 L/h; (b) concentration of starting materials 300 g/L/passage flow rate of 90 L/h; (c) concentration of starting materials 600 g/L/passage flow rate of 30 L/h; (d) concentration of starting materials 600 g/L/passage flow rate of 90 L/h; and FIG. 8 represents scanning electron microscopy (SEM) photographs of calcium zincate crystals obtained according to the process of the invention using 2 mm balls and the following parameters: (a) concentration of starting materials 300 g/L/passage flow rate of 30 L/h; (b) concentration of starting materials 300 g/L/passage flow rate of 90 L/h; (c) concentration of starting materials 600 g/L/passage flow rate of 30 L/h; (d) concentration of starting materials 600 g/L/passage flow rate of 90 L/h.

The Applicant focused on the development of a novel process for manufacturing calcium zincate crystals that is suitable for use on an industrial scale and that especially allows the following synthesis:

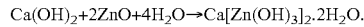

$$Ca(OH)_2 + 2ZnO + 4H_2O \rightarrow Ca[Zn(OH)_3]_2 \cdot 2H_2O.$$

In particular, one subject of the present invention is a process for manufacturing calcium zincate crystals which comprises at least the following steps:
(1) placing in suspension at least: calcium hydroxide ($Ca(OH)_2$) and zinc oxide (ZnO) or a precursor thereof such as $ZnO_2$ or $Zn(OH)_2$ or a mixture thereof, with water, known as the "starting suspension", the mass ratio of (water):(calcium hydroxide+zinc oxide, a precursor thereof or a mixture thereof) being greater than or equal to 1, preferably ranging from 2 to 15 and in particular ranging from 3 to 5;
(2) milling said starting suspension at an ambient temperature of less than or equal to 50° C., preferably less than or equal to 35° C., in a three-dimensional wet-phase microball mill for a residence time of less than or equal to 15 minutes, preferably less than or equal to 1 minute, and especially ranging from 5 to 25 seconds and in particular from 10 to 20 seconds;
(3) recovering at the mill outlet a suspension of calcium zincate crystals, and
(4) optionally, said suspension of calcium zincate crystals is concentrated or dried so as to obtain a powder of calcium zincate crystals.

The Applicant has thus developed a process which, unexpectedly, makes it possible to manufacture calcium zincate crystals in a very short time (reaction time of less than or equal to 15 minutes and generally less than or equal to 1 minute), in a single step, at ambient temperature (the process does not require any particular heating step), and does so with minimum energy and water consumption (non-polluting), and also in an excellent yield.

As will be demonstrated in the tests below, the process of the invention furthermore makes it possible, surprisingly, to obtain calcium zincate crystals of excellent quality, i.e. very pure and with a fine and well-controlled particle size.

The process according to the invention also has the advantages of having a very low cost price (the starting materials used are effectively widely available, non-polluting and inexpensive) and of having excellent reproducibility, which further distinguishes it from the processes described in the prior art. The process according to the invention also has the advantage of being able to be performed continuously. Now, these characteristics are important for an application on an industrial scale.

In addition, despite the extensive research conducted on the synthesis of calcium zincate crystals since 1958, none has suggested the abovementioned process and in particular a step of milling in a three-dimensional microball mill using a starting suspension comprising at least: calcium hydroxide ($Ca(OH)_2$) and zinc oxide (ZnO), a precursor thereof or a mixture thereof, and of doing so in an excess of water.

To better understand the process that is the subject of the invention, a three-dimensional microball mill capable of allowing the production of calcium zincate crystals, and thus forming part of the invention, will first be described below with reference to FIGS. 1 and 2.

As illustrated in FIG. 1, a three-dimensional microball mill 1 comprises at least:
a stationary milling chamber 2 of cylindrical general shape extending along a longitudinal axis XX, said chamber 2 being at least partly filled with said microballs (not shown) and comprises: at a first end 3 at least one inlet 5 serving to introduce said starting suspension, and at a second end 4, an outlet 6 comprising a separating means 7 that is capable of evacuating only the calcium zincate suspension thus formed in said chamber 2; and
an agitator 8, arranged in the stationary milling chamber 2, which is in the form of a rod elongated along the longitudinal axis XX, said agitator 8 being capable of placing the microball/starting suspension assembly in motion.

In particular, the inlet 5 is generally connected to a peristaltic pump (not shown). This pump delivers the starting suspension contained, for example, in a container, such as a tank, into the milling chamber 2 via the inlet 5. The pump also makes it possible, during the functioning of the three-dimensional mill, to convey this starting suspension at a certain flow rate that is adjustable, referred to hereinbelow as the "passage flow rate". This passage flow rate also forms a stream in the milling chamber 2 for entraining the starting suspension from the inlet 5 to the outlet 6.

The outlet 6 of the milling chamber 2 in particular comprises the system 7 for separating the microballs from the final suspension predominantly comprising the calcium zincate crystals, water and optionally the remaining unreacted starting materials. This separating means 7 may be a screen whose orifices have a size smaller than that of the microballs or a separating slit whose width is also adapted to retain the microballs in the chamber 2.

The inner wall 9 of the milling chamber 2 comprises, according to a first embodiment, a smooth inner surface. However, according to an implementation variant that will be described below, fingers 11 may be arranged on this inner surface 9.

As mentioned above, the agitator 8 is placed inside the milling chamber 2 and, in addition to the passage flow rate, said agitator also places the starting suspension in motion.

In particular, the agitator 8 is capable of rotating about the axis X via a rotary shaft (14, FIG. 2) to give the starting suspension, in the milling chamber 2, a turbulent motion and thus to effect intense blending between this starting suspension and the microballs present in the chamber 2 along the inner wall 9 of this chamber 2.

In order to improve this blending, the agitator 8, and similarly the inner wall 9 of the chamber 2, may have various possible configurations represented, for example, in FIG. 2.

According to a first configuration illustrated in FIG. 2a, the agitator 8 comprises along its elongated rod disks 10 arranged perpendicular thereto. They may vary in number from 2 to 8, preferably from 2 to 5. These disks 10 make it possible, firstly, to improve the milling of the starting suspension by better blending the microballs, and, secondly, to accelerate the reaction time.

According to a second configuration illustrated in FIG. 2b, the agitator 8 may also comprise along its rod one or more disks 10 arranged perpendicularly, and which are also capable of cooperating with fingers 11 arranged perpendicularly, relative to the inner wall 9 of the chamber 2. A finger is especially in the form of a ring which extends perpendicularly from the wall 9. For this configuration, the disks 10 and the fingers 11 are arranged in a staggered manner, i.e. the disks 10 and the fingers 11 are arranged alternately in the chamber 2. In addition, the thickness of the rod 8 is increased relative to the preceding configuration (FIG. 2a) so that the periphery of the disks 10 is close to the inner wall 9 and so that the periphery of the fingers 11 is close to the periphery of the rod of the agitator 8. Thus, in this configuration, the volume of the chamber is reduced relative to the preceding configuration, consequently allowing better blending between the starting suspension, the microballs and the inner wall 9 of the chamber 2.

The volume of the chamber 2 may also be reduced as is illustrated in FIG. 2c. In this configuration, the agitator 8 has an outside diameter slightly smaller than the inside diameter of the chamber 2, thus forming an annular chamber 12 of low volume arranged between the outer wall of the agitator 8 and the inner wall 9 of the chamber 2. The microballs (not shown) are placed in this annular chamber 12. During the functioning of this configuration, the starting suspension is introduced via the inlet 5 at a certain flow rate, and then passes through the annular chamber 12 up to the outlet 6 while at the same time being blended by the microballs.

In general, the mill that is suitable for performing the process according to the invention comprises a milling chamber with a diameter of from 75 mm to 300 mm for a length of from 80 mm to 900 mm and an agitator ranging from 60 mm to 260 mm in size. Thus, the volume of the milling chamber ranges from 0.35 L to 600 L, preferably from 0.35 L to 62 L.

The geometry of the milling chamber and of the agitator may be adjusted by a person skilled in the art as a function of the desired amount of calcium zincate crystals, and also of the desired reaction time. For example, it is also possible for the milling chamber 2 to comprise an accelerator so as to improve the milling of the starting suspension.

In addition, the microballs housed in the milling chamber 2, and which are suitable for use in the process according to the invention, are substantially spherical and have a mean diameter ranging from 0.05 mm to 4 mm, preferably from 0.2 to 3 mm, in particular from 0.3 to 2 mm, and typically 0.5 to 1 mm. Preferably, the diameter of the microballs is less than or equal to 1 mm.

They are preferentially chosen from microballs of high hardness and relatively good resistance to abrasion.

In particular, the microballs have a Vickers hardness measured according to standard EN ISO 6507-1 of greater than or equal to 900 HV1, preferably ranging from 900 HV1 to 1600 HV1, typically ranging from 1000 to 1400 HV1.

Advantageously, they have a high real mass per unit volume. In general, the microballs according to the invention have a real mass per unit volume of greater than or equal to 2 $g/cm^3$, in particular ranging from 2 to 15 $g/cm^3$, preferably from 3 to 12 $g/cm^3$, and typically from 4 to 10 $g/cm^3$.

Thus, the microballs according to the invention may be ceramic microballs (zirconium oxide $ZrO_2$, zirconium silicate $ZrSiO_4$); steel microballs, tungsten carbide microballs, glass microballs or a combination thereof.

Preferably, the microballs are ceramic since they do not generate any pollution as a result of their wear.

In particular, the microballs are made of zirconium oxide.

Optionally, the zirconium oxide microballs may be stabilized with another oxide, such as cerium oxide, yttrium oxide and/or silicon.

By way of examples, the following compositions, summarized in table 1 below, are suitable for forming the microballs according to the invention:

TABLE 1

| Composition of the microballs | HV1 hardness | Real mass per unit volume ($g/cm^3$) | Manufacturer |
| --- | --- | --- | --- |
| Zirconium oxide microballs stabilized with cerium oxide 80% $ZrO_2$ 20% CeO | 1180 | ≥6.10 | Saint-Gobain (Zirmil ®Y Ceramic Beads) or EIP (Procerox ® ZO Cer) |
| Zirconium oxide microballs stabilized with yttrium 95% $ZrO_2$ <5% $Al_2O_3$ Remainder: $Y_2O_3$ | 1250 | ≥5.95 | EIP (Procerox ® ZO (Y)) |
| Zirconium oxide microballs stabilized with yttrium and silicon: 78% $ZrO_2$, 12% $SiO_2$, 5% $Al_2O_3$ and 4% $Y_2O_3$ | >700 | >4.80 | Saint-Gobain (ER120 Ceramic Beads) |
| Zirconium silicate $ZrSiO_4$ microballs | ≥800 | >6.5 | Saint-Gobain (Rimax Ceramic Beads) |

TABLE 1-continued

| Composition of the microballs | HV1 hardness | Real mass per unit volume (g/cm³) | Manufacturer |
|---|---|---|---|
| Glass microballs | 500 | >3.76 | — |
| Steel microballs | 700 | >7.7 | — |

In particular, the microballs represent, by volume relative to the total volume of the stationary chamber 2, from 50% to 85%, preferably from 55% to 70%.

By way of example, the three-dimensional wet-phase microball mill that is suitable for performing the process according to the invention may correspond to mills sold by the companies WAB, Dyno-Mill range: Multi Lab, ECM and KD, Netzch, for example Labstar LS1, or Alpine Hosokawa, for example Agitated Media Mill AHM.

The manufacturing process according to the invention will now be described more explicitly below.

As indicated previously, the manufacture of the calcium zincate crystals according to the invention first comprises (1) a step of placing in suspension at least the following compounds: calcium hydroxide ($Ca(OH)_2$) and zinc oxide (ZnO) or a precursor thereof or a mixture thereof in a large excess of water. The suspension obtained is referred to hereinbelow as the "starting suspension".

For the purposes of the invention, a zinc oxide (ZnO) precursor may correspond to $ZnO_2$ or to a zinc hydroxide, such as $Zn(OH)_2$.

The starting suspension may thus comprise, in addition to calcium hydroxide ($Ca(OH)_2$), ZnO, or a precursor thereof (such as $ZnO_2$ or $Zn(OH)_2$), or a mixture thereof, i.e. a mixture of ZnO+precursor(s) or a mixture of precursors (such as $ZnO+ZnO_2$; $ZnO+ZnO_2+Zn(OH)_2$; or $ZnO_2+Zn(OH)_2$; etc.).

Preferably, the starting suspension comprises ZnO.

For the rest of the description, the characteristics relating to ZnO are understood as characteristics relating to ZnO, or a precursor thereof, or a mixture thereof.

The starting suspension is conventionally prepared by mixing the starting materials ($Ca(OH)_2$+ZnO) with water in a suitable device, such as a container or a tank, equipped with a stirring system (such as a magnetic stirrer, stirring paddles, etc.). The device and the stirring system may be adapted by a person skilled in the art as a function of the amount of calcium zincate crystals to be manufactured.

In particular, calcium hydroxide and zinc oxide, a precursor thereof, or a mixture thereof are mixed, preferably, in stoichiometric proportion in the starting suspension. In particular, for a starting mixture comprising calcium hydroxide and zinc oxide, the CA/Zn mole ratio will be 1/2 to perform the reaction:

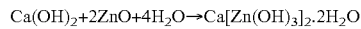

$$Ca(OH)_2 + 2ZnO + 4H_2O \rightarrow Ca[Zn(OH)_3]_2 \cdot 2H_2O$$

This corresponds, in mass proportions, to 74 kg of $Ca(OH)_2$ per 162.8 kg of ZnO, i.e. 31.25% of $Ca(OH)_2$ and 68.75% of ZnO.

Needless to say, it is possible to depart substantially from the stoichiometric proportion, for example by mixing from 27 to 35%, by weight, of $Ca(OH)_2$ with, respectively, from 73 to 65% by weight of ZnO, relative to the total weight of $Ca(OH)_2$+ZnO, if, for example, a calcium zincate composition containing an excess either of slaked lime or of zinc oxide is desired.

In contrast with the prior art publications, water is not only present in the starting suspension in stoichiometric proportion. Said suspension in fact comprises a large excess of water. The mass ratio of (water):(calcium hydroxide+zinc oxide) is greater than or equal to 1, preferably ranges from 2 to 15 and in particular ranges from 3 to 5. This excess of water allows not only the synthesis of the calcium zincate crystals, but also promotes the placing in motion of the microballs of the mill for better milling of the starting suspension and thus better synthesis of the calcium zincate crystals.

In general, the starting materials of the starting suspension are in powder form.

The calcium hydroxide that is suitable for use in the present invention preferably has a particle size of less than or equal to 100 µm and preferably less than or equal to 10 µm, and in particular the particle size ranges from 0.01 µm to 1 µm. The calcium hydroxide of CAS number: 1305-62-0 and sold, for example, by the company Sigma Aldrich, with a purity of greater than or equal to 96%, is suitable for performing the process of the invention.

The zinc oxide that is suitable for use in the present invention is also in powder form and generally has a particle size of less than or equal to 100 µm and preferably less than or equal to 10 µm, and in particular the particle size ranges from 0.01 µm to 1 µm. The zinc oxide of CAS number: 1314-13-2 and sold, for example, by the company Selectra, with a purity of greater than or equal to 99.9%, is suitable for performing the process of the invention.

Preferably, the calcium hydroxide and the zinc oxide are of high purity, generally greater than or equal to 90%, in particular greater than or equal to 95% and typically greater than or equal to 99%, or even greater than or equal to 99.9%.

To minimize the presence of calcium carbonate in the hydroxide, it is advantageously appropriate to start with quicklime prepared by calcination of calcium carbonate at a temperature slightly above the industrial standard, for example 1050° C.

Once the starting suspension is prepared, it is conveyed to the three-dimensional microball mill 1 generally by means of the peristaltic pump at a flow rate that is adjustable via the inlet 5. The peristaltic pump allows mixing of the starting suspension to be continued before entry into the chamber 2. In addition, as indicated previously, this pump makes it possible to introduce the starting suspension into the chamber 2 at a controlled passage flow rate.

Generally, the starting suspension is introduced at a passage flow rate of from 10 to 130 L/h, preferably from 20 to 100 L/h and typically from 30 to 90 L/h.

Once the starting suspension is introduced into the chamber 2, the milling step (2) begins.

Under the effect of the stream created by the passage flow rate, the starting suspension travels through the stationary chamber 2 from the inlet 5 to the outlet 6, while at the same time being placed in motion by the agitator 8 which allows intense blending of this suspension with the microballs and, where appropriate, with the disks 10, the fingers 11, etc., along the inner wall 9 of the chamber 2.

The rotation speed of the agitator may range, for example, from 4 to 20 Pi rad/s, preferably from 4 to 8 Pi rad/s.

The residence time of the starting suspension is less than or equal to 15 minutes, preferably less than or equal to 1 minute, and ranges especially in the mill from 5 to 25 seconds and in particular from 10 to 20 seconds. It is in fact inherent to the apparent volume of the balls and to the passage flow rate. For example, if the total apparent volume of the balls is 270 cm$^3$ (balls with an apparent mass per unit volume of 3.7 g/cm$^3$) and if the rate of introduction of the suspension is 30 L/h, i.e. 8.3 cm$^3$/s, then the residence time of the suspension in the chamber 2 is estimated at about 32 seconds. Consequently, the residence time may be advantageously adjusted, for example, by controlling the apparent mass per unit volume of the microballs, and also the passage flow rate.

The term "apparent volume" means the volume of the microballs including the interstitial air between the balls. The apparent mass per unit volume is the ratio between the mass of the microballs and the apparent volume.

In addition, by modifying the size of the microballs and the passage flow rate, coarser or finer crystals may be obtained. For example, finer milling may be obtained if the flow rate of the starting suspension is slowed down.

The milling step may be performed in continuous mode or in batch mode in one or more passes (pendular mode or recirculation mode).

When it is performed in batch mode, the number of passes of the "starting" suspension may be from 1 to 10, preferentially from 1 to 5 (i.e. after a first pass, the suspension is recovered at the outlet 6 and it is reinjected again, by means of the pump, into the chamber 2 via the inlet 5 to allow a second pass). In particular, the number of passes of the starting suspension is 1.

Specifically, the Applicant has noted that a single pass in the microball mill, despite a very short residence time, made it possible to obtain at the outlet 6 a suspension very predominantly comprising calcium zincate crystals (especially when the starting materials are in stoichiometric proportion), of very satisfactory purity and size.

Thus, this milling step will preferably be performed in continuous mode.

Advantageously, this milling step proceeds at an ambient temperature of less than or equal to 50° C., i.e. usually at an ambient temperature ranging from 15° C. to 45° C., in particular from 18° C. to 35° C. and in general is about 20° C. to 25° C. Specifically, the process according to the invention does not require any particular heating in order to manufacture the calcium zincate crystals, in contrast with the teaching disclosed in the prior art.

Once the milling step has been performed, (3) the calcium zincate suspension is recovered at the outlet 7 of the mill 1 and is optionally (4) concentrated or dried so as to obtain a calcium zincate powder.

According to one implementation variant, the calcium zincate suspension may be dried in the open air. Specifically, it appeared that the carbonation reaction is very slow between calcium zincate and atmospheric $CO_2$.

According to another implementation variant, the calcium zincate suspension may be dried by baking or by calcination, such as at a temperature of from 100 to 400° C. for 1 to 4 hours.

The final product is generally stored until the time of use in the form of an aqueous paste or mixed with a solvent. It may also be dried and stored in a leaktight container.

As will be demonstrated in the tests below, homogeneous calcium zincate crystals, which are generally lozenge-shaped, are obtained.

In particular, the length of the major axis of these crystals ranges from 0.1 to 30 μm, preferably from 1 to 25 μm (long diagonal).

Advantageously, the length of the minor axis (the shortest diagonal) ranges from 0.05 to 20 μm, preferentially from 0.11 to 12 μm.

The calcium zincate crystals obtained via the process of the invention generally have the following population distributions as a function of their particle size measured with a liquid-route laser particle size analyzer:

5 μm≤$D_x$50≤13 μm, preferably 8 μm≤$D_x$50≤13 μm and 10 μm≤$D_x$90≤25 μm, preferably 12 μm≤$D_x$90≤22 μm.

In addition, as mentioned above, the characteristics of the calcium zincate crystals (size, thickness, etc.) may be adjusted, as a function of the needs of the intended use, by varying a number of parameters, such as the passage flow rate, the diameter of the microballs or the water content in the starting suspension.

The present invention also relates to a suspension or powder of calcium zincate crystals obtained according to the process defined above, characterized in that the calcium zincate crystals are in microlozenge form and have the following population distributions as a function of their particle size measured with a liquid-route laser particle size analyzer:

5 μm≤$D_x$50≤13 μm, preferably 8 μm≤$D_x$50≤18 μm and 10 μm≤$D_x$90≤25 μm, preferably 12 μm≤$D_x$90≤22 μm.

The calcium zincate crystals according to the invention in fact have, intrinsically, a microlozenge form whose opposite angles are equal and whose consecutive angles are complementary to 180°. As measured in FIG. 3, these angles approximately have values of 125°+/−5° and 55°+/−5°. This intrinsic form is also confirmed on all the images in FIGS. 6, 7 and 8 with the exception of the fractures occasionally leading to only a lozenge fragment.

In particular, it was found that the length of the major axis (long diagonal) of the calcium zincate crystals preferably ranges from 0.1 to 30 μm, in particular from 1 to 25 μm, and typically ranges from 1 to 20 μm; whereas the length of the shortest axis (shortest diagonal) may range from 0.05 to 20 μm, preferentially from 0.11 to 12 μm. Consequently, the process according to the invention makes it possible to obtain microlozenges, contrary to the processes described in the prior art which make it possible only to obtain calcium zincate crystals in lozenge form (not in microlozenge form) in which the length of the major axis is greater than 30 μm and is generally greater than or equal to 60 μm.

It was also found that the calcium zincate crystals have a lamellar form whose thickness is very much less than the length thereof. This means that the shorter the length of the crystals, the more their specific surface area increases, and the more their properties are improved for the uses mentioned below.

The Applicant has thus discovered, surprisingly, that the calcium zincate crystals obtained via the process according to the invention differ from the calcium zincate crystals obtained via the processes described in the prior art especially on the basis of their particle size distribution and their microlozenge form. These characteristics are induced by the process according to the invention and cannot be obtained by simple milling of calcium zincate crystals, for example in a mill. Specifically, such milling would especially have the effect of destroying the lozenge form.

In addition, and as is mentioned above, these characteristics have the advantage of increasing the specific surface area of the powder or suspension of calcium zincate crystals, thus making it possible to improve its properties, in particular for the uses mentioned below. It was found that the specific surface area (determined via the BET method known to those skilled in the art) of the calcium zincate crystals obtained according to the process of the invention is generally at least 6 m$^2$/g, preferably at least 10 m$^2$/g, in particular at least 12 m$^2$/g and typically at least 15 m$^2$/g, such as 17 m$^2$/g.

For the purposes of the invention, "a specific surface area of at least 6 m$^2$/g" covers the following values or any interval between the following values: 6; 7; 8; 9; 10; 11; 12; 13; 14; 15; 16; 17; etc.

A subject of the present invention is also the uses of the powder or suspension of calcium zincate crystals obtained according to the abovementioned process.

Firstly, calcium zincate may be used as main element in the composition of the zinc anode of an alkaline electrochemical generator. To reduce the formation of zinc deposits, which are often dendritic, spongy or pulverulent during the recharging phases of the zinc electrode, it is in fact necessary to limit the solubility of the zinc oxide in the alkaline electrolyte, which is generally constituted mainly of potassium hydroxide.

Many mixtures of zinc oxide and calcium hydroxide have been studied for this purpose: the results, which are relatively disappointing, are clearly explained, for example, in the publication by R. Jain entitled "Development of long-lived high-performance zinc-calcium/nickel oxide cells" appearing in the "Journal of Applied Electrochemistry 22 (1992): 1039-1048".

To improve the situation, WO 98/44579 proposed incorporating into the active mass of the electrode, not a mixture of zinc oxide and calcium hydroxide, but directly calcium zincate, which is transformed in situ during the successive charging/discharging cycles of the generator. This direct incorporation has the advantage of ensuring uniform distribution of the calcium zincate even before the first placing in service of the battery, which facilitates its initial formation. The maximum possible number of cycles may be increased, as is demonstrated in the publication by Jingxian Yu entitled "A study of calcium zincate as negative electrode material for secondary batteries" appearing in the "Journal of Power Sources 103(2001): 93-97".

Also, WO 2006/0322208 teaches that the performance in rapid discharge regime may be significantly improved if the mean size of the crystals is reduced to 30 μm. However, to reduce the size of the crystals used, the authors had to improve their chemical process by seeding with much smaller crystals, preferably prepared via mechanosynthesis. Since mechanosynthesis processes are difficult to transpose to the industrial scale, said document demonstrates the advantage of finer powders but does not provide a solution for their production. The process according to the invention, which makes it possible industrially to obtain powders whose mean size is smaller than 30 μm, provides the desired solution and should even allow a greater improvement in the performance of the generator.

Thus, the use of calcium zincate crystals in powder or suspension obtained according to the process of the invention and having a mean size of less than 20 μm, or even 10 μm, would make it possible to obtain better performance, especially if this improvement is combined with that which may be obtained by adding titanium nitride powder to the composition of the electrode as is mentioned in WO 03/015197 A2 and WO 2004/013064 A2.

Next, the calcium zincate powder or suspension may be used to manufacture a heterogeneous catalyst for the production of biodiesel as is mentioned in the publication by J M Rubio Caballero, "Calcium zincate as precursor of active catalysts for biodiesel production under mild conditions", Applied Catalysis B: Environmental 91(2009) 339-346; in WO 2010/112641 and in the publication by Zeljka Kesic "Mechanochemical preparation and characterisation of CaO.ZnO used as catalyst for biodiesel synthesis", published in the book "Applied Catalyst A: General 427-428 (2012) 58-65 (Elsevier).

In particular, calcium zincate may be used for the production of biodiesel by reacting methanol with plant oils, the calcium zincate being calcined beforehand at a temperature of greater than or equal to 400° C., preferably at a temperature of between 500° C. and 700° C., in the presence, for example, of air, a neutral gas, a mixture of a neutral gas and oxygen or a mixture of nitrogen and oxygen. This forming operation proved particularly stable when functioning in methanol. Since the catalytic capacity of the calcined calcium zincate certainly depends on the specific surface area of the powder used for its implementation, the powders obtained via the process according to the invention should thus be particularly efficient.

Finally, the calcium zincate powder or suspension may be used as an antifungal product. This use is particularly advantageous for providing long-lasting protection of limestone monuments, for example the Mayan monuments in Mexico, which are exposed to a hot and humid atmosphere. Specifically, the growth of fungi impairs the surface layer of these monuments, as is explained in the publication by N. M. Gomez-Ortiz "Antifungal activity of Ca[Zn(OH)$_3$]$_2$.2H$_2$O coatings for the preservation of limestone monuments: an in vitro study"; published in the book "International Biodeterioration & Biodegradation 91 (2014) 1-8".

Other antifungal applications may be envisaged, especially for protecting plants.

EXAMPLES

The description of the tests below is given as a purely nonlimiting illustration.

A° Characterization

SEM

Scanning electron microscopy (SEM) was performed on a Zeiss EVO MA 15 machine, with secondary and backscattered electrons (chemical contrast) with a primary beam of 5 to 20 kV.

To perform the tests by SEM, the calcium zincate crystal suspensions were dried beforehand in air at 50° C. so as to obtain a powder.

XRD

The X-ray diffractometry (XRD) spectra were acquired with a D8 Advance Series II diffractometer sold by the company Bruker using CuKα1 radiation (0.15406 nm) in Bragg-Brentano configuration.

The detector used is a LynxEye 1D detector from Bruker. The aperture angle of the detector is 3° (150 bands).

The XRD measurements were performed between 10° and 40° (at the 2θ scale) with an increment of 0.008° (1 s/increment).

To perform the XRD tests, the calcium zincate crystal suspensions were also predried in air at 50° C., so as to obtain a powder.

Measurement of the Liquid-Route Particle Size

The liquid-route particle size measurements were performed with a laser particle size analyzer from the company Malvern on the Mastersizer 3000E model.

For this measurement, 5 cm³ of samples of calcium zincate crystal suspension to be analyzed were predispersed in a container with a diameter of 40 mm using a 28 kHz/40 kHz ultrasonic generator equipped with a sonotrode 20 mm in diameter.

This measurement gives the volume distribution (as a percentage) of the particles of the sample for each particle size class in μm (which corresponds to the longest length of the calcium zincate crystals).

B° Process for Preparing the Test Samples

Apparatus

The tests were performed in a Dyno Mill MultiLab microball three-dimensional mill from the company Willy A. Bachofen AG, which contains 1 kg of microballs.

The microballs are made of zirconium oxide and have a diameter of 0.5, 1.0 or 2.0 mm. The characteristics of the microballs used for the tests are summarized in table 2 below:

TABLE 2

| Balls | 500 μm | 1.0 mm | 2.00 mm |
|---|---|---|---|
| Composition (mass %) | 93% $ZrO_2$ 5% $Y_2O_3$ 2% others | 93% $ZrO_2$ 5% $Y_2O_3$ 2% others | 93% $ZrO_2$ 5% $Y_2O_3$ 2% others |
| Specific mass per unit volume | 6 g/cm³ | 6 g/cm³ | 6 g/cm³ |
| Apparent mass per unit volume | 3.7 kg/L | 3.7 kg/L | 3.7 kg/L |
| Vickers hardness | 1250 HV1 | 1250 HV1 | 1250 HV1 |

The 500 μm microballs are especially sold under the brand name Zirmil® Y Ceramic Beads by the company Saint-Gobain.

The milling chamber of the mill has a capacity of 309 mL and is filled, on a volume basis, relative to its total volume and as a function of the tests, to 80% with the microballs described above.

In functioning, the microballs are placed in agitation by an agitator at a rotation speed of 2890 rpm. The agitator also comprises two polyurethane mixing disks 64 mm in diameter.

Starting Materials

For the tests, the starting materials are: calcium hydroxide (Ca(OH)₂) with a purity≥96% sold by the company Sigma Aldrich, and zinc oxide of purity≥99.9% sold by the company Selectra and demineralized water.

General Procedure Used for the Tests:

To perform each test below, the following steps were performed:

a starting suspension is prepared in a beaker using calcium hydroxide and zinc oxide, in stoichiometric proportion, in demineralized water, i.e. at a "starting materials/demineralized water" concentration of 300 g/L or 600 g/L; the starting suspension is then stirred using a magnetic stirrer;

it is then conveyed, via a peristaltic pump at an adjustable flow rate, to the Dyno Mill MultiLab mill described above: the passage flow rates tested in the mill are 30 l/h or 90 l/h corresponding to respective residence times of 12 s and 4 s;

the starting suspension is then milled in the mill comprising microballs 0.5 mm; 1 mm or 2 mm in diameter for a certain time (which depends as indicated above on the passage flow rate of the starting suspension) at ambient temperature (20-25° C.), thus making it possible, at the mill outlet, to obtain a suspension of calcium zincate crystals;

finally, the suspension of calcium zincate crystals is recovered.

Figure 4:
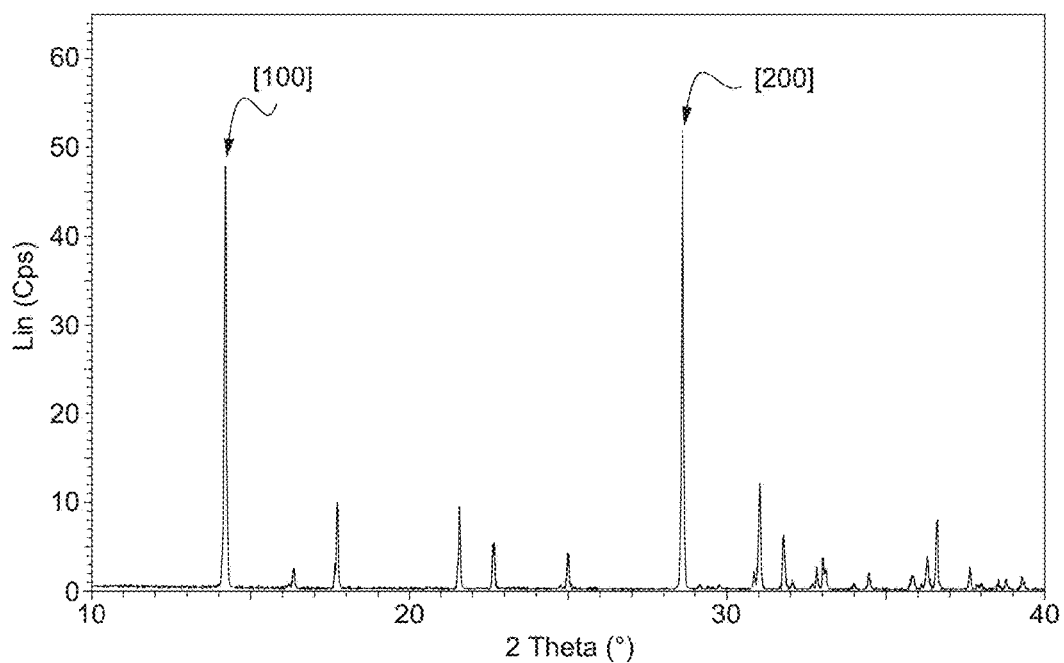
FIG. 4 is an X-ray diffractometry (XRD) spectrum of calcium zincate crystals obtained under the same experimental conditions as those of FIG. 3.

C° Example 1: Characterization of the Calcium Zincate Crystals Obtained (FIGS. 3 and 4)

The calcium zincate crystals obtained according to the process of the invention were prepared for this example according to the general procedure described above and using:

a starting suspension comprising a concentration of 300 g/L;

a passage flow rate of 30 L/h;

with balls 500 μm in diameter:

and performing only one pass through the mill.

The suspension of calcium zincate crystals was then recovered and dried in the open air at 50° C.

SEM and XRD tests were then performed. The results of these tests are given, respectively, in FIGS. 3 and 4.

As may be seen in FIG. 3, the calcium zincate crystals obtained according to the process of the invention have, surprisingly, after only one pass through the microball mill and thus a residence time of 12 seconds, a characteristic lozenge form (instead of 48 hours according to the prior art processes). According to this test, the length of the major axis of this lozenge, i.e. its longest diagonal, is about 19-20 μm, and the length of the other diagonal is about 10.47 μm. As may be seen in FIG. 3, the two characteristic angles of the lozenges are 55.2° and 126.9° (thus, two consecutive angles together measure substantially 180°).

With reference to FIG. 4, it is seen that the lines of the XRD spectrum obtained are entirely in agreement with those of the reference spectrum for calcium zincate, known to those skilled in the art (JCPDS 024-0222), both for their angular positions and for their relative intensities, i.e.:

the presence is noted of the two main peaks (crystallographic planes [100] and [200]) about, respectively, 14.15° and 28.6°, the peak [100] effectively having an intensity of about 90% of the peak [200];

all the other significant peaks are present at the expected angles, such as 16.1°/16.3°/17.6°/21.6°/22.6°/24.7°/24.9°/29.1°/29.7°/30.8°/31.0°/31.7°/32.0°/32.8°/32.8°/33.0°/36.5° with substantially the expected intensities.

This XRD spectrum also shows that the sample analyzed has excellent purity. Specifically, no contamination is detected:

the main peak for ZnO (according to JCPDS 036-1451) which is at 29.4°, is barely visible on the spectrum;

the main peaks for Ca(OH)₂ (according to JCPDS 044-1481), which are at 18.0°/28.7°/34.1° do not appear either;

and the main peak for $CaCO_3$ (according to JCPDS 005-0586), which is at 29.4°, is barely visible.

Finally, just like for the other characteristics, the calcium zincate crystals obtained via the process according to the invention have a mass per unit volume (g/cm³) which is in agreement with that given in the literature, i.e. 2.60 g/cm³.

In conclusion, the process of the invention makes it possible immediately to obtain very pure calcium zincate crystals of characteristic lozenge form.

Figure 5:
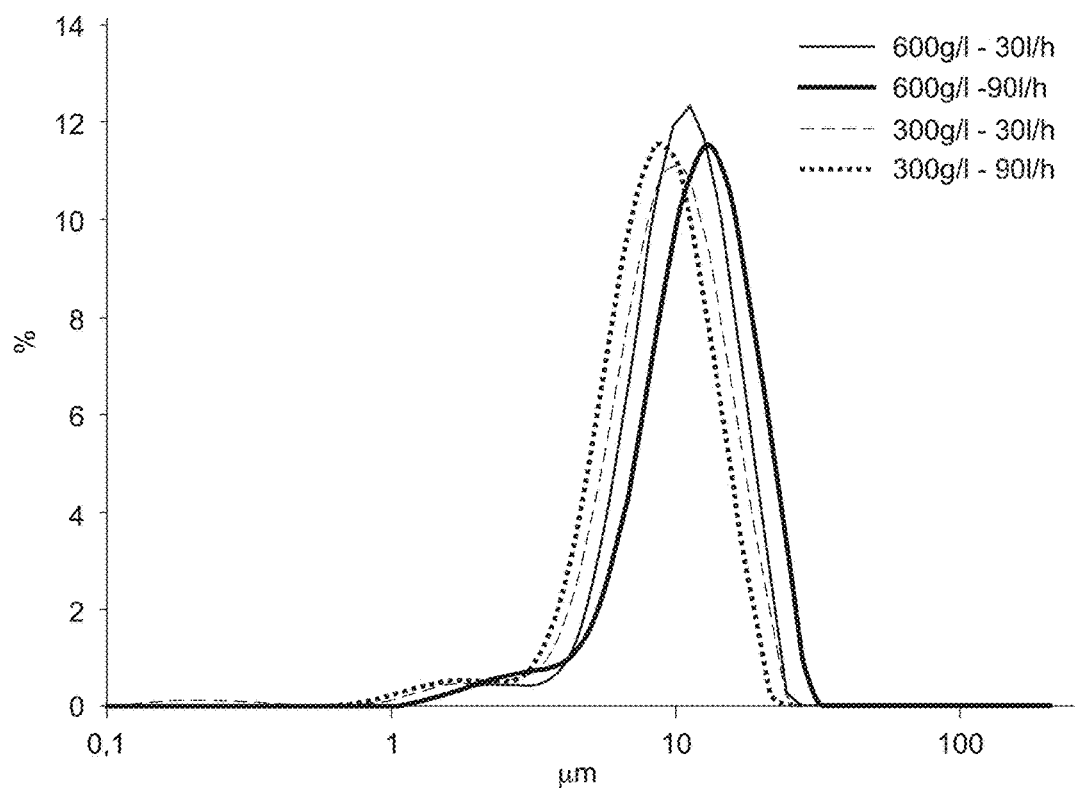
FIG. 5 is a graph of the three-dimensional distribution of the large axis of the calcium zincate crystals obtained according to the process of the invention by varying the concentration of the starting materials in the starting suspension (300 g/L or 600 g/L) and/or the passage flow rate (30 L/h or 90 L/h)

D° Example 2: Particle Size of the Calcium Zincate Crystals as a Function of the Concentration of the Starting Materials and of the Passage Flow Rate (FIG. 5)

For this example, various concentrations of starting materials (calcium hydroxide and zinc oxide) were tested, along with various passage flow rates, in order to check their impact on the particle size of the crystals obtained and in particular on the size of the major axis of the lozenge-shaped calcium zincate crystals.

Thus, the calcium zincate crystals tested were synthesized according to the general procedure mentioned above and using the following parameters:

a starting suspension comprising a concentration of 300 g/L or of 600 g/L;
a passage flow rate of 30 L/h or 90 L/h;
with balls 500 µm in diameter:
and performing only one pass through the mill.

The result of these tests is illustrated in FIG. 6.

Thus, this FIG. 6 shows that, irrespective of the parameter variations (concentration at 300 g/L or 600 g/L or passage flow rate of 30 L/h or 90 L/h), the size of the longest diagonal of the lozenge-shaped calcium zincate crystals is substantially constant.

In particular, the following particle size distribution is obtained (table 3):

TABLE 3

| Tests | Dx(10) (µm) | Dx(50) (µm) | Dx(90) (µm) |
|---|---|---|---|
| 1) 300 g/L - 30 L/h | 4.75 | 9.02 | 15.1 |
| 2) 300 g/L - 90 L/h | 5.03 | 9.97 | 16.9 |
| 3) 600 g/L - 30 L/h | 6.12 | 11.1 | 17.9 |
| 4) 600 g/L - 90 L/h | 6.36 | 12.8 | 21.1 |
| Mean | 5.57 | 10.7 | 17.8 |
| Standard deviation | 0.792 | 1.61 | 2.50 |

Thus, the process according to the invention makes it possible to obtain homogeneous zincate crystals of small sizes (between 4 and 20 µm) with absence of large crystals, irrespective of the concentration of the starting materials and of the passage flow rate.

E° Example 3: Influence of the Diameters of the Balls (FIGS. 6 to 8)

The aim of this example is to determine whether the size of the balls used for performing the process has an influence on the quality of the calcium zincate crystals obtained.

As for the tests of Examples 1 and 2, the calcium zincate crystals tested were synthesized according to the general procedure mentioned above and in particular using the following parameters:

a starting suspension comprising a concentration of 300 g/L or 600 g/L;
a passage flow rate of 30 L/h or 90 L/h;
with balls 500 µm, 1 mm or 2 mm in diameter:
and performing only one pass in the mill.

The results of these tests are illustrated in FIGS. 6 to 8.

From the SEM images, it is seen that the conversion of the calcium hydroxide and zinc oxide into calcium zincate is very close to 100% irrespective of the size of the balls used.

However, when the process is performed with balls having a mean diameter of 1 mm or 2 mm, a few residues of unconverted material in the form of a white powder are seen. It is estimated that the proportion of these residues is about 1% by mass. Thus, balls with a diameter<1 mm make it possible to obtain better results under the conditions stated above.

It is also seen that balls with a diameter of 0.5 mm make it possible to obtain crystals of larger sizes (the size measured being the size of the major axis of the calcium zincate lozenges).

Also, as for test 2, it is noted that the size of the major axis is less than 20 µm with total absence of large crystals.

In conclusion, the size of the balls used, when this size is less than or equal to 2 mm, has little impact on the size of the calcium zincate crystals obtained. However, a ball size<1 mm makes it possible to obtain better synthesis of the calcium zincate in a single pass of the starting suspension through the mill.

F° Conclusion

Thus, it has been demonstrated that, for all the tests, a water-insoluble powder was obtained. After control by XRD analysis, it was seen that this powder corresponded to calcium zincate crystals (all the XRD spectra produced by the Applicant show an integral transformation of the starting compounds into calcium zincate, the spectra in fact indicate only the lines corresponding to calcium zincate, with only a few residual traces of the initial compounds).

The images obtained by scanning electron microscopy reveal the lozenge-shaped crystals, characteristic of calcium zincate. It also turns out that the powder obtained is mainly constituted of well-formed crystals for which the length of the major axis is generally less than 20 µm.

In addition, the laboratory mill makes it possible, for example, to produce 54 kg/h of calcium zincate crystals. This figure can be multiplied by ten by adding an accelerator accessory. Also, industrial versions of the mill exist using, for example, up to 100 kg of balls. With this type of mill, it would consequently be possible to manufacture several tonnes per hour of calcium zincate.

The invention claimed is:

1. A process for manufacturing calcium zincate crystals which comprises at least the following steps:
   (1) placing in suspension at least: calcium hydroxide ($Ca(OH)_2$) and zinc oxide (ZnO) or a precursor thereof, or a mixture thereof, with water, referred to as the starting suspension the mass ratio of (water):(calcium hydroxide+zinc oxide, a precursor thereof or a mixture thereof) being greater than or equal to 1;
   (2) milling said starting suspension at an ambient temperature of less than or equal to 50° C., in a three-dimensional wet-phase microball mill for a residence time of less than or equal to 15 minutes; and
   (3) recovering at the mill outlet a suspension of calcium zincate crystals.

2. The process as claimed in claim 1, in which the mass ratio of (water):(calcium hydroxide+zinc oxide, a precursor thereof or a mixture thereof) is ranging from 2 to 15.

3. The process as claimed in claim 2, in which the mass ratio of (water):(calcium hydroxide+zinc oxide, a precursor thereof or a mixture thereof) is ranging from 3 to 5.

4. The process as claimed in claim 1, in which the calcium hydroxide and the zinc oxide or a precursor thereof or a mixture thereof are mixed in stoichiometric proportion corresponding to a Ca/Zn mole ratio=1/2.

5. The process as claimed in claim 1, in which the length of the major axis of the calcium zincate crystals ranges from 0.1 μm to 30 μm.

6. The process as claimed in claim 1, in which the calcium zincate crystals have the following particle size distributions: 5 μm≤$D_x50$≤13 μm and 10 μm≤$D_x90$≤20 μm measured with a liquid-route laser particle size analyzer.

7. The process as claimed in claim 1, in which the microballs are spherical and have a mean diameter ranging from 0.05 mm to 4 mm.

8. The process as claimed in claim 7, in which the microballs are spherical and have a mean diameter ranging from 0.2 to 3 mm.

9. The process as claimed in claim 8, in which the microballs are spherical and have a mean diameter ranging from 0.5 to 1 mm.

10. The process as claimed in claim 1, in which the microballs have a Vickers hardness measured according to standard EN ISO 6507-1 of greater than or equal to 900 HV1.

11. The process as claimed in claim 10, in which the microballs have a Vickers hardness measured according to standard EN ISO 6507-1 which is ranging from 900 HV1 to 1600 HV1.

12. The process as claimed in claim 11, in which the microballs have a Vickers hardness measured according to standard EN ISO 6507-1 which is ranging from 1000 to 1400 HV1.

13. The process as claimed in claim 1, in which the microballs have a real mass per unit volume ranging from 2 to 15 g/cm$^3$.

14. The process as claimed in claim 1, in which the milling is performed at an ambient temperature ranging from 15° C. to 45° C.

15. The process as claimed in claim 14, in which the milling is performed at an ambient temperature ranging from 18° C. to 35° C.

16. The process as claimed in claim 1, in which the three-dimensional microball mill comprises at least:
a stationary milling chamber of cylindrical general shape extending along a longitudinal axis XX, said chamber being at least partly filled with said microballs and comprises: at a first end at least one inlet serving to introduce said starting suspension, and at a second end, an outlet comprising a separating means that is capable of evacuating only the calcium zincate suspension thus formed in said chamber; and
an agitator, arranged in the stationary milling chamber, which is in the form of a rod elongated along the longitudinal axis XX, said agitator being capable of placing the microball/starting suspension assembly in motion.

17. The process as claimed in claim 16, in which the microballs represent, by volume, relative to the total volume of the stationary chamber, from 50% to 85%.

18. The process as claimed in claim 1, in which the three-dimensional microball mill functions continuously.

19. The process as claimed in claim 1, wherein the residence time in step (2) is from 5 to 25 seconds.

20. The process as claimed in claim 1, further comprising:
obtaining a powder of calcium zincate crystals by concentrating or drying said suspension of calcium zincate crystals.

* * * * *